(12) United States Patent
Katsura et al.

(10) Patent No.: US 7,632,971 B2
(45) Date of Patent: Dec. 15, 2009

(54) METHOD OF CRYSTALLIZATION OF BICALUTAMIDE

(75) Inventors: Tadashi Katsura, Toyonaka (JP); Tadashi Mizuno, Ibaraki (JP); Nobushige Itaya, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/571,956

(22) PCT Filed: Jul. 13, 2005

(86) PCT No.: PCT/JP2005/013346

§ 371 (c)(1),
(2), (4) Date: Mar. 12, 2007

(87) PCT Pub. No.: WO2006/006736

PCT Pub. Date: Jan. 19, 2006

(65) Prior Publication Data

US 2007/0238900 A1    Oct. 11, 2007

(30) Foreign Application Priority Data

Jul. 14, 2004  (JP) .............................. 2004-207709

(51) Int. Cl.
*C07C 233/05*  (2006.01)
*C07C 255/50*  (2006.01)

(52) U.S. Cl. ...................................... 564/162; 558/413

(58) Field of Classification Search ................. 564/162; 558/413

See application file for complete search history.

(56) References Cited

U.S. PATENT DOCUMENTS

| 4,636,505 A | 1/1987 | Tucker |
| 7,102,026 B2 * | 9/2006 | Dolitzky et al. ............. 558/413 |
| 2003/0191337 A1 | 10/2003 | Shintaku et al. |
| 2004/0044249 A1 | 3/2004 | Dolitzky et al. |
| 2004/0063782 A1 | 4/2004 | Westheim |
| 2005/0202092 A1 | 9/2005 | Shantze et al. |
| 2006/0183934 A1 | 8/2006 | Shintaku et al. |

FOREIGN PATENT DOCUMENTS

| EP | 0 100 172 A1 | 8/1984 |
| WO | WO 2004/009057 A1 | 1/2004 |
| WO | WO 2004/100944 A1 | 11/2004 |

OTHER PUBLICATIONS

Tucker et al., Nonsteroidal Antiandrogens. Synthesis and Structure—Activity Relationships of 3-Substituted Derivatives of 2-Hydroxypropionanilides, Journal of Medical Chemistry, 1988, pp. 954-959, vol. 31, No. 5.

* cited by examiner

*Primary Examiner*—Shailendra Kumar
(74) *Attorney, Agent, or Firm*—Foley & Lardner LLP

(57) ABSTRACT

The present invention provides a method of crystallization of bicalutamide comprising adding an acetone solution containing bicalutamide to water; crystals of bicalutamide wherein particle size distribution of the crystals is 1 to 10 μm of $Dp_{10}$, 10 to 25 μm of $Dp_{50}$ and 25 to 100 μm of $Dp_{90}$, and the crystals are obtainable by the method described above; and crystals of bicalutamide, wherein particle size distribution of the crystals is 1 to 3 μm of $Dp_{10}$, 2 to 5 μm of $Dp_{50}$ and 5 to 15 μm of $Dp_{90}$.

10 Claims, No Drawings

METHOD OF CRYSTALLIZATION OF BICALUTAMIDE

This application is a 371 of PCT/JP05/13346, filed Jul. 13, 2005.

FIELD OF THE INVENTION

The present invention relates to a method of crystallization of bicalutamide, and to bicalutamide crystals having a particle size distribution excellently suitable for formulation.

BACKGROUND OF THE INVENTION

Bicalutamide represented by the formula (I):

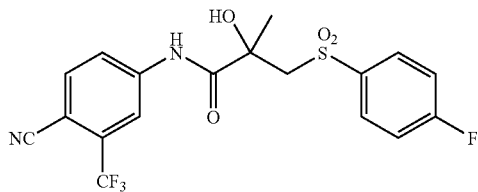

is reported as a useful compound having an antiandrogen activity (EP0100172-A, EP1462442-A, US2004/0044249A1, and the like), and is also an important compound currently employed for various drug applications.

Formulations of bicalutamide are provided in forms of tablets and capsules, and such formulations must be strictly administered under the standards required therefor to stably exhibit medicinal effects of the bicalutamide. Especially, as particle sizes and specific surface areas of bicalutamide crystals used for a bulk significantly affect medicinal effects and side effects, it is expected to be important to employ bicalutamide crystals having suitable particle sizes and specific surface areas. Consequently, developments of bicalutamide crystals having such suitable particle sizes and specific surface areas and methods of efficiently producing such crystals are desired.

EP1462442-A discloses a method for producing bicalutamide crystals of which shapes are regulated by dissolving bicalutamide in ethyl acetate followed by addition of heptane or the like to crystallize. The bicalutamide crystals thus obtained, however, have the particle sizes of 45.6 μm of $Dp_{10}$, 90.7 μm of $Dp_{50}$ and 177.6 μm of $Dp_{90}$, according to the measurement results conducted by the present inventors.

US2004/0044249A1 describes a method of crystallizing bicalutamide by adding acetone into an aqueous dispersion of bicalutamide crystals in a range of dissolving the bicalutamide crystals, followed by leaving the solution standing at a room temperature. This method, however, may decrease efficiency because of the requirement of a large amount of solvent to completely dissolve bicalutamide crystals as well as decrease recovery rate due to the great volume of the solvent. Besides, since the particle sizes of crystals thus obtained are large, this method, as well as that of EP1462442-A, is not necessary the way of efficiently producing suitable bicalutamide crystals.

SUMMARY OF THE INVENTION

The objects of the present invention are to provide bicalutamide crystals having a specific particle size distribution and specific surface area, and a novel crystallization method for efficiently producing the bicalutamide crystals; that is, to provide bicalutamide crystals having a specific form, and a method for obtaining bicalutamide, which is economical, excellent in stability of product quality, and industrially applicable.

The present inventors have diligently studied to solve the above-mentioned problems, and then achieved the present invention.

That is, the present inventions are as follows:

<1> A method of crystallization of bicalutamide comprising adding an acetone solution containing bicalutamide to water.

<2> The method according to <1>, wherein the amount of acetone in the acetone solution containing bicalutamide is 2 to 10 g per 1 g of bicalutamide.

<3> The method according to <1> or <2>, wherein the amount of water is 0.5 to 10 g per 1 g of acetone.

<4> The method according to any of <1> to <3>, wherein the temperature of water at the time of the addition is 0 to 30° C.

<5> Crystals of bicalutamide wherein particle size distribution of the crystals is 1 to 10 μm of $Dp_{10}$, 10 to 25 μm of $Dp_{50}$ and 25 to 100 μm of $Dp_{90}$, and the crystals are obtainable by a method comprising adding an acetone solution containing bicalutamide to water.

<6> The crystals of bicalutamide according to <5>, wherein specific surface area of the crystals is 0.4 to 1 $m^2/g$.

<7> Crystals of bicalutamide, wherein particle size distribution of the crystals is 1 to 3 μm of $Dp_{10}$, 2 to 5 μm of $Dp_{50}$ and 5 to 15 μm of $Dp_{90}$.

<8> The crystals of bicalutamide according to <7>, wherein specific surface area is 1 to 5 $m^2/g$.

<9> The crystals of bicalutamide according to <7> or <8>, which is obtainable by one time milling of crystals of bicalutamide obtained by a crystallization method obtainable by a method comprising adding an acetone solution containing bicalutamide to water.

<10> The crystals according to <9>, wherein the one time milling is carried out by a mill selected from a jet-mill, a hammer-crasher, a ball-mill and a disk-crasher or by a combination thereof.

DESCRIPTION OF PREFERRED EMBODIMENTS

Crystallization Method

The method of crystallization of bicalutamide of the present invention includes adding an acetone solution containing bicalutamide to water.

The acetone solution containing bicalutamide (hereinafter, referred to as the said acetone solution), for example, can be prepared by adding bicalutamide into an acetone solvent and dissolving. The amount of the acetone is typically 2 to 10 g per 1 g of bicalutamide, and preferably 3 to 7 g. Taking account the solubility of bicalutamide to the acetone solvent into consideration, the acetone solution is preferably maintained usually at 10 to 50° C., and preferably 20 to 30° C., if necessary, with heating.

Alternatively, the acetone solution, for example, may be prepared by concentrating an acetone solution containing low content of bicalutamide. In this case, the concentration may be carried out to adjust the amount of acetone within the ranges mentioned above. Further, after the concentration, it is preferred that the concentrated solution is maintained usually at 10 to 50° C., and preferably 20 to 30° C. to avoid precipitation of bicalutamide crystals.

In the present invention, water is used usually at 0 to 30° C., and preferably 0 to 15° C. in order to obtain fine crystals. As a method adding the said acetone solution to water is adopted in the present crystallization method, the acetone concentration in the water (crystals precipitated liquid) becomes higher with the addition of the said acetone solution. As long as the final amount of water in the crystals precipitated liquid after the addition of the said acetone solution is 0.5 g or more per 1 g of acetone, acceptable crystals in quality and yield can be obtained. Though it is preferred in view of the simplicity to put the whole amount of water in a vessel before adding the said acetone solution, it can be adopted, for example, a method that one half of the whole amount of water is put into a vessel before the addition of the said acetone solution, the remainder is dividedly added during the addition of the said acetone solution. In the present invention, the water to which the said acetone solution is added includes not only water alone but also bicalutamide crystals precipitated liquid obtained by adding the said acetone solution to water, in other words, an aqueous liquid containing acetone, soluble amount of bicalutamide and precipitated bicalutamide crystals, as long as acceptable crystals in quality and yield can be obtained. The method of addition of the said acetone solution may be the addition by continuous supplying or dropwise supplying. Though it depends on a scale of reaction volume, the time for addition is usually 10 minutes to 10 hours. The agitation speed is not particularly limited as long as being capable of dispersing the said acetone solution into the water, for example, preferably 200 to 500 rpm in a scale of 200 ml flask.

After finishing the addition of the said acetone solution into water, the agitation is preferably further conducted. The agitation is carried out usually at 0 to 30° C., and preferably 0 to 15° C., and the agitation time is usually 10 minutes to 5 hours, and more preferably 10 minutes to 1 hour.

And then, by filtrating the agitated solution, intended crystals of bicalutamide can be collected. The filtration method is not particularly limited, reduced pressure filtrations, pressured filtrations, centrifugal filtrations, and the like may be used alone or as a combination thereof. Furthermore, the crystal may be washed with a mixture of acetone and water or water during the filtration. The crystals collected may be dried through circulation drying, by reduced pressure drying, and the like.

Thus precipitated bicalutamide crystals can be controlled in smaller particle size ranges than those obtained by the conventional methods. For example, the particle sizes determined by a laser diffractometry can be preferably controlled in the range of 1 to 10 μm of $Dp_{10}$, 10 to 25 μm of $Dp_{50}$, and 25 to 100 μm of $Dp_{90}$, and more preferably 2 to 6 μm of $Dp_{10}$, 10 to 20 μm of $Dp_{50}$, and 25 to 80 μm of $Dp_{90}$. The specific surface area of the crystals can be controlled in the range of 0.4 to 1 $m^2/g$.

To obtain such particle size distributions, applying the crystallization method of the present invention is critical, and if any procedure other than that of the present invention is applied, for example, crystallization is performed by a step adding water into an acetone solution of bicalutamide, bicalutamide crystals result in larger particle size distributions.

The bicalutamide crystals obtained by the crystallization method of the present invention have small particle sizes, this allows to introduce the crystals to crystals having much finer particle size distributions and larger specific surface area by a less-loading and simple milling. The milling method is not particularly limited, usually a way of finely breaking solid with a mill. The mill includes, for example, a jet-mill, a hammer-crasher, a ball-mill, a disk-crasher, and the like, and a combination thereof, and preferably a jet-mill to obtain fine particles.

(Particle Size Distribution)

The bicalutamide crystals obtained by such milling exhibit a particle size distribution of 1 to 3 μm of $Dp_{10}$, 2 to 5 μm of $Dp_{50}$, and 5 to 15 μm of $Dp_{90}$, and more preferably 1 to 2 μm of $Dp_{10}$, 2.5 to 5 μm of $Dp_{50}$, and 5 to 12 μm of $Dp_{90}$. The bicalutamide crystals having such particle size distribution ranges are expected to have suitably excellent solubility and absorption rate.

In the invention, $Dp_n$ is a unit referring to a particle size of crystal, and n is a value covering from 1 to 100. For example, $Dp_{10}$ is defined as a diameter of the particle where particles are accumulated from the one having a smaller size and reach to the accumulated particle volume of 10%.

(Method of Measuring Particle Size Distribution)

Add 1000 mL of water to 5 g of Triton X-100, mix well. Add 0.1 g of bicalutamide and sonicate for 15 minutes, the filter using 0.45 μm membrane filter and use this solution as the dispersant. Rinse the dispersion unit and the measurement instrument with the dispersant and replace it in the instruments with the fresh one, then measure background. After weighing, suspend about 0.05 g of bicalutamide crystals in the 20 ml of dispersant and sonicate for 5 minutes, and make up with the dispersant to 100 mL. Redisperse this suspension with a pipet and pour this sample into the dispersion unit so that an obscuration is 10.0 to 20.0%. After the stabilizing period of 12 minutes, start the measurement under the following condition. Determine 10% diameter, 50% diameter, and 90% diameter according to an integrated distribution curve to be $Dp_{10}$, $Dp_{50}$ and $Dp_{90}$, respectively.

Measurement Condition:
Instrument model: Laser diffraction particle size analyzer Mastersizer 2000 (Malvern)
Dispersion unit: Hydro2000S
Stirrer speed of dispersion unit: 2300 rpm
Particle Refraction Index of sample: 1.670 Absorption: 0.001
Dispersant Refraction Index: 1.330
Analysis model: General purpose
Calculation sensitivity: Enhanced
Particle shape: Irregular
Size range: 0.020-2000.000 μm
Measurement integration period: 12 seconds
Backgroupd integration period: 12 seconds (Specific Surface Area)

The bicalutamide crystals thus obtained also have a specific surface area of 1 to 5 $m^2/g$, and preferably 2 to 4 $m^2/g$, therefore being expected to be a bulk for drugs suitably having absorbability and solubility.

The specific surface area in the invention is defined as a surface area per 1 g of particles, and represented by a value measured by the following method.

(Method for Measuring Specific Surface Area)

A sample is deaerated overnight in a vacuum dryer at 40° C. as a pre-treatment before being subjected to a measurement. The measurement is conducted as follows: a given amount of an absorbing gas (nitrogen gas) is absorbed by a sample, the values of a relative pressure (P/PO) and an absorbed gas volume are determined in each absorption step, and then a specific surface area is calculated according to the BET equation using the values. COULTER™ SA3100™ Series Surface Area and Pore size Analyzer is used as a measurement device. After measuring the sample mentioned above, the specific surface area at around the relative pressure of 0.05 to 0.2 is calculated.

The present invention will be specifically explained according to the following Examples, but should not be construed to be limited thereto.

Example 1

In a flask having 5l capacity, bicalutamide (240 g, 0.558 mol) and acetone (1200 g) were sequentially added, and then agitated and dissolved at 20 to 30° C. After dissolution, the mixed solution was added dropwise into 3600 g of water cooled at 5° C. for 2 hours (dropping rate: about 12.5 ml/minute). And then, the solution was agitated at 5° C. for 30 minutes, followed by collecting bicalutamide as crystals with filtration to dry under a reduced pressure. (236.6 g, yield 98.6%) Purity 100%

A particle size distribution and specific surface area of the crystals obtained were measured.

(Measurement of Particle Size Distribution)

With using the above-mentioned laser diffraction particle size distribution analyzer (Mastersizer 2000 (Malvern)), a particle size distribution was measured under the same conditions mentioned above.

As the results, the particle size distribution of the above-mentioned crystals was 5.3 μm of $Dp_{10}$, 14.5 μm of $Dp_{50}$, and 30.6 μm of $Dp_{90}$.

And then, the crystals obtained above were milled at one time with a mill of spiral jet-mill 50AS (Hosokawa Micron Group).

The Milling Conditions were:

Supplied air 0.2 Mpa,

Diameter of injector nozzle f 0.8 mm,

Milling air pressure 0.4 Mpa,

Diameter of milling nozzle f 0.8 mm,

The number of nozzles 4, and

Feed rate 997 g/hr.

The particle size distribution of the crystals obtained by one time milling was 1.8 μm of $Dp_{10}$, 4.2 μm of $Dp_{50}$, and 10.5 μm of $Dp_{90}$ according to the results measured by the measurement method mentioned above under the same conditions.

Furthermore, the specific surface area of the crystals obtained by one time milling was measured with the COULTER™ SA3100™ Series Surface Area and Pore size Analyzer mentioned above under the same conditions mentioned above.

The specific surface area calculated at around the relative pressure of 0.05 to 0.2 was 1.8 m²/g.

(Results)

According to the above Example, the method of the present invention was able to provide bicalutamide crystals of which particle size distribution was more suitable to formulation than the conventional.

Comparative Example 1

In a four neck flask having a capacity of 200 ml, 4'-cyano-3-(4-fluorophenylthio)2-hydroxy-2-methyl-3'-trifluoromethylpropionanilide (12.2 g, 30.6 mmol) produced by a method described in EP1462442-A and ethyl acetate (20 ml) were sequentially added, and then agitated under an ice cooling (2 to 7° C.). Ethyl acetate solution of monoperphthalic acid (166.58 g, net amount 22.31 g, 122.5 mmol) was added dropwise at a temperature of 10° C. or less, and then agitated for 1 hour. 20% Potassium hydroxide solution (117.5 g) was added dropwise and then subjected to a phase separation. The water layer was extracted with ethyl acetate (30 ml), and the organic layers were combined, and the combined organic layer was washed with an aqueous solution dissolving 3.0 g of sodium pyrosulfite in de-ionized water (30 ml), dried with magnesium sulfate, and then concentrated under a reduced pressure. The residue was added with 66 ml of ethyl acetate and then heated up to at 60° C. 40 ml of n-Heptane was added dropwise at a temperature of 60 to 65° C. for 40 minutes. After finishing the dropwise addition, the solution was gradually cooled down to a room temperature (about 20 to about 25° C.), followed by filtration to collect bicalutamide (12.24 g, yield 91.2%) as crystals. Purity 99.97%.

A particle size distribution of the crystals obtained was measured with the laser diffraction particle size distribution analyzer under the conditions described in Example 1, resulting in 45.6 μm of $Dp_{10}$, 90.7 μm of $Dp_{50}$, and 177.6 μm of $Dp_{90}$.

The bicalutamide crystals obtained by the above method was milled at two times with CT-401 (ATOMIZER) (manufactured by Fuji Paudal Co., Ltd.) [rotation number=8000 rpm, screen=2 mm, feed rate=62 rpm, (1.4 L/M), hammering numbers=12]

(Measurement of Particle Size Distribution)

A particle size distribution was measured with the same method as in Example 1

The particle size distribution of the crystals obtained by two times milling was 3.1 μm of $Dp_{10}$, 15.9 μm of $Dp_{50}$, and 57.8 μm of $Dp_{90}$.

Comparative Example 2

In a flask having a capacity of 200 ml, bicalutamide (12 g, 28 mmol) and 60 g of acetone were sequentially added, and then agitated at a temperature of 50 to 55° C. After confirming the dissolution, 60 g of water was added dropwise with a dropping funnel at the same temperature for 30 minutes. Thereafter, bicalutamide crystals (0.05 g, 0.12 mmol) were added, and then 30 g of water was added dropwise through a dropping funnel at the same temperature for 40 minutes. The solution was maintained at the same temperature for 1.5 hours, cooled down to 5° C. for 9 hours, and then maintained at the cooled temperature for 6 hours. And then, bicalutamide was collected as crystals by filtration, followed by drying under a reduced pressure (11.95 g, yield 99.6). Purity 100%.

A particle size distribution and specific surface area of the crystals obtained were measured with the same methods as in Example 1.

The particle size distribution obtained was 39.5 μm of $Dp_{10}$, 119.6 μm of $Dp_{50}$, and 273.1 μm of $Dp_{90}$, and the specific surface area was 0.2 m²/g.

The present invention can provide a novel crystallization method for efficiently producing bicalutamide crystals of which particle sizes are finer than those of the conventional. And, the bicalutamide crystals obtained by the said crystallization method, due to having smaller particle sizes compared with that of conventional crystals, can be efficiently introduced, by a less-loading and simple milling, to bicalutamide crystals having particle size distribution and specific surface area which are expected for excellent in solubility and absorption rate.

The invention claimed is:

1. A method of crystallization of bicalutamide comprising adding an acetone solution containing bicalutamide to water, wherein the temperature of water at the time of the addition is 0 to 30° C.

2. The method according to claim 1, wherein the amount of acetone in the acetone solution containing bicalutamide is 2 to 10 g per 1 g of bicalutamide.

3. The method according to claim 1, wherein the amount of water is 0.5 to 10 g per 1 g of acetone.

4. Crystals of bicalutamide wherein particle size distribution of the crystals is 1 to 10 μm of $Dp_{10}$, 10 to 25 μm of $Dp_{50}$ and 25 to 100 μm of $Dp_{90}$, and the crystals are obtainable by a method comprising adding an acetone solution containing bicalutamide to water.

5. The crystals of bicalutamide according to claim 4, wherein specific surface area of the crystals is 0.4 to 1 $m^2/g$.

6. Crystals of bicalutamide, wherein particle size distribution of the crystals is 1 to 3 μm of $Dp_{10}$, 2 to 5 μm of $Dp_{50}$ and 5 to 15 μm of $Dp_{90}$.

7. The crystals of bicalutamide according to claim 6, wherein specific surface area is 1 to 5 $m^2/g$.

8. The crystals of bicalutamide according to claim 6, which is obtainable by one time milling of crystals of bicalutamide obtained by a crystallization method obtainable by a method comprising adding an acetone solution containing bicalutamide to water.

9. The crystals according to claim 8, wherein the one time milling is carried out by a mill selected from a jet-mill, a hammer-crasher, a ball-mill and a disk-crasher or by a combination thereof.

10. The method according to claim 1, wherein the temperature of water at the time of the addition is 0 to 15° C.

\* \* \* \* \*